United States Patent [19]
Gelman

[11] Patent Number: 6,146,414
[45] Date of Patent: Nov. 14, 2000

[54] MEDICAL GRAFT AND CONSTRUCTION OF THE SAME

[76] Inventor: Martin L. Gelman, 50 W. Elm St., Hopkinton, Mass. 01748

[21] Appl. No.: 08/994,902

[22] Filed: Dec. 19, 1997

[51] Int. Cl.[7] .................................................. A61F 2/00
[52] U.S. Cl. ................................................... 623/1
[58] Field of Search ............................... 623/1, 12

[56] References Cited

U.S. PATENT DOCUMENTS

| | | | |
|---|---|---|---|
| 3,648,295 | 3/1972 | Palma | 623/1 |
| 5,700,287 | 12/1997 | Myers | 623/1 |
| 5,713,859 | 2/1998 | Finch | 623/1 |
| 5,769,882 | 6/1998 | Fogarty | 623/1 |
| 5,800,514 | 9/1998 | Nunez | 623/1 |

OTHER PUBLICATIONS

A Study of Patency and Durability of IMPRA Carbon–Coated Synthetic Prostheses in Dogs, C. R. Bard, United States, (2 pages).
Bleedless Coup—Brochure which demonstrates vascular grafts, Jun. 1996, W. L. Gore, United States, (7 pages).
IMPRA Carboflex—Brochure demonstrating stepped grafts, 1996, C. R. Bard, United States, (29 pages).
Lifespan Cross Reference List, Sep. 1996, Baxter, United States, (11 pages).
Clinical Summary for IMPRA Grafts, C. R. Bard, United States, (3 pages).
Modified PTFE Grafts, Oct. 1992, Tsuchida et al., United States, (8 pages).

*Primary Examiner*—Michael J. Milano
*Attorney, Agent, or Firm*—Lambert & Associates; Randolph P. Calhoune; Scott B. Garrison

[57] ABSTRACT

A bio-compatible graft for use in a patient. The graft contains a plurality of expanded regions which provide greater access to the graft and additional area within which to cannulate the patient with a needle, as for dialysis treatment. The expanded regions will provide greater graft lifetime and increase the target area available for cannulation. Additionally shields are provided at a posterior aspect of each of the regions. The shields serve as a indicator to an operator that further cannulation of the needle into the patient will cause the needle to protrude through the posterior wall of the graft. This indication is had by the excess force necessary to push the needle into the shield once the shield is contacted by the needle tip.

7 Claims, 2 Drawing Sheets

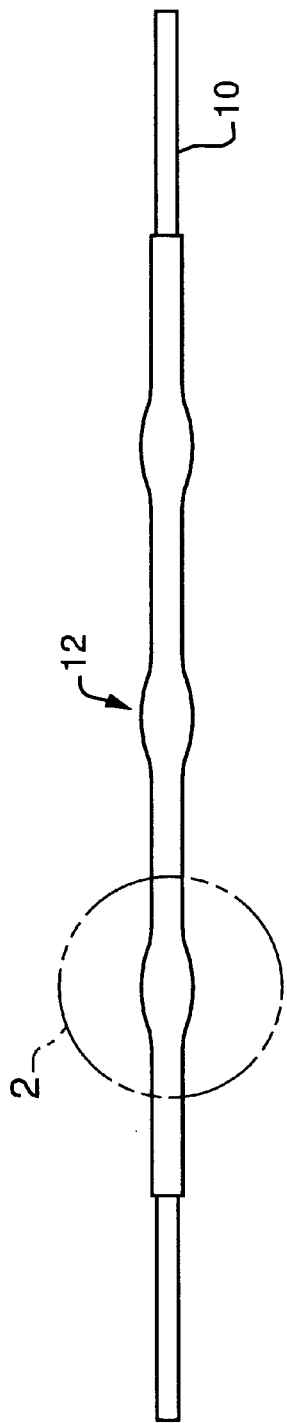
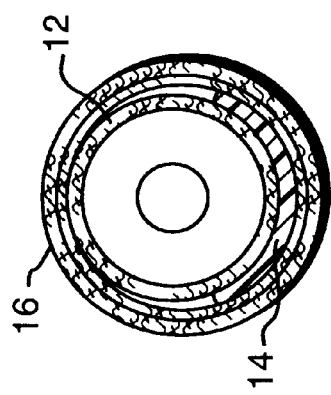

MEDICAL GRAFT AND CONSTRUCTION OF THE SAME

BACKGROUND OF THE INVENTION

The present invention relates to the field of medical dialysis. More particularly, it relates to an improvement in grafts designed to reduce the frequency of graft failure. Although the invention can be adapted to a wide range of uses, it is especially well-suited for use in the dialysis field. Other uses could be, but are not limited to, intravenous hyperalimentation, frequent prolonged venous access as with chemotherapy, plasmapheresis, leukopheresis, repetitive venipuncture, etc.

Currently in excess of 200,000 patients undergo dialysis therapy, 85 percent of whom undergo hemodialysis. This process involves removing toxic waste products from the blood by convection and diffusion through a semipermeable membrane known as an artificial kidney. Dialysis has been available for patients with kidney failure for over 30 years. Widespread use of the process began in the United States in 1972 with the passage of the End-Stage Renal Disease Program under Medicare legislation. The treatment of chronic kidney failure requires this dialysis process to remove the toxic chemicals which accumulate in the blood as a result of normal metabolic processes of the body. This is done by exposing the waste filled blood to a clean dialysis solution via a semipermeable membrane in the artificial kidney. This process permits uni-directional osmotic difflusion of the noxious waste substances to flow from the blood side of the membrane to the dialysate side after which the waste filled dialysate is disposed. To enable adequate volumes of blood to be exposed to the dialysis membrane the patient's veins must be enlarged by creating conduits between arteries and veins. These artificial conduits, called grafts, allow a high rate of blood to flow through them and when connected with dialysis needles deliver large volumes of blood to the dialysis membrane through the dialysis machine.

This process occurs three times per week, or thirteen times a month and lasts for approximately three to four hours per session. The grafts are usually constructed of a synthetic material such as Dacron, Gortex, polyurethane, PTFE, silicone, or other materials known in the art. The life expectancy of these grafts varies from six months to two years and is limited by stenosis, infection, and clotting. Regardless of the graft material used, all current graft designs include a cylindrical tube fashioned to fit a circular, elliptical, or marquis-shaped anastomosis from an artery to a vein. Straight, curved, or U-shaped grafts are available for a variety of connections, depending upon the position of the desired graft. Nevertheless, the working portion of all grafts are cylindrical tubes with a variety of shapes and a variety of fixed luminal diameters throughout the graft's length.

Regardless of the graft design, two major types of problems often occur. The first is difficulty with cannulation to access the graft and the second is bleeding from the graft site. The first problem is that the graft is too narrow or too deep to cannulate and the dialysis staff cannot accurately place the needles into the graft to achieve adequate blood flow. This problem is typically caused by; the luminal diameter being too small in cross-section or the graft being too deep to appreciate its anatomical location within the patient. Inaccurate needle placement is the usual result.

The second problem, that of leakage of blood from either a hole or laceration of the graft, is a result of erroneous needle cannulation. A common problem encountered with graft bleeding is hemorrhage below the graft, so called infragraft hemorrhage, which occurs when the needle is placed too far into the graft resulting in backwall perforation. This occurs in an estimated 25–30 percent of all cannulations. This type of perforation is not immediately obvious to the naked eye and can cause sufficient hemorrhage around the graft to occlude the graft from extreme pressure caused by the hemorrhage. This usually leads to complete loss of the graft.

SUMMARY OF THE INVENTION

What is needed is a graft which overcomes the above deficiencies. The present Applicant has such a solution which is both novel and non-obvious. Applicant's device solves both the problems associated with narrowed lumina and the problems associated with backwall perforation of the graft.

To solve the problems associated with narrowed lumina, the Applicant has created a graft with a plurality of expanded areas or regions formed into a portion of the graft. Though grafts are made to allow cannulation at any spot along their length, it is well known that nurses or technicians routinely cannulate those regions with the easiest access. If the graft is too narrow, too deep, or otherwise has poor flow, then no area has easy access.

The Applicant has found that a graft incorporating a number of purposely expanded areas would increase the intraluminal area and allow for easier cannulation. These expanded areas would be of similar wall thickness as the remainder of the graft but be incorporated into the body of the graft. The expanded portion of the graft would allow for easier cannulation as a larger target with a larger luminal diameter. The Applicant has also determined that providing multiple expanded sites actually provides a plurality of expanded sites from which to choose thereby allowing rotation of usable sites to avoid recannulating the same area during each treatment which often leads to graft stenosis and failure. By way of example, if four expanded sites were available, then six different two-needle combinations would be available for rotation. This would prolong graft life. Alternatively, in the unlikely event that all of the expanded sections were unavailable for cannulation, the non-expanded portions could be used for cannulation as is done presently with currently used grafts.

A second feature of this graft solves the problem of backwall perforation. The Applicant has situated a firm back shield into the inferior aspect of the expanded graft segments to prevent perforation of the back wall. The shield should be made of a bio-compatible material such as polyethylene. However other rigid and semi-rigid bio-compatible materials are suitable as well. This back shield would reduce the frequency of infragraft perforations, estimated to occur in 25 to 30 percent of all cannulations. With the back shield, the needle tip would hit the hard surface of the shield thereby signaling the operator to discontinue placing pressure on the needle thus avoiding through and through perforation of the graft.

Therefore it is an object of the present invention to provide a graft which by the combination of a larger surface area resulting from expanded portions of the graft and incorporation of a back wall shield is both safer to use and longer lasting.

BRIEF DESCRIPTION OF THE DRAWINGS

The novel features considered characteristic of the invention are set forth in the appended claims. The invention itself, however, both as to its construction and its method of operation, together with additional objects and advantages thereof, will best be understood from the following description of the specific embodiments when read and understood in connection with the accompanying drawings.

FIG. 1 is a front plan view of one embodiment of a graft in accordance with the present invention;

FIG. 3 is a sectional view along line 1—1 of FIG. 2 of the present invention.

DETAILED DESCRIPTION OF THE PREFERRED EMBODIMENT

Figure 2:
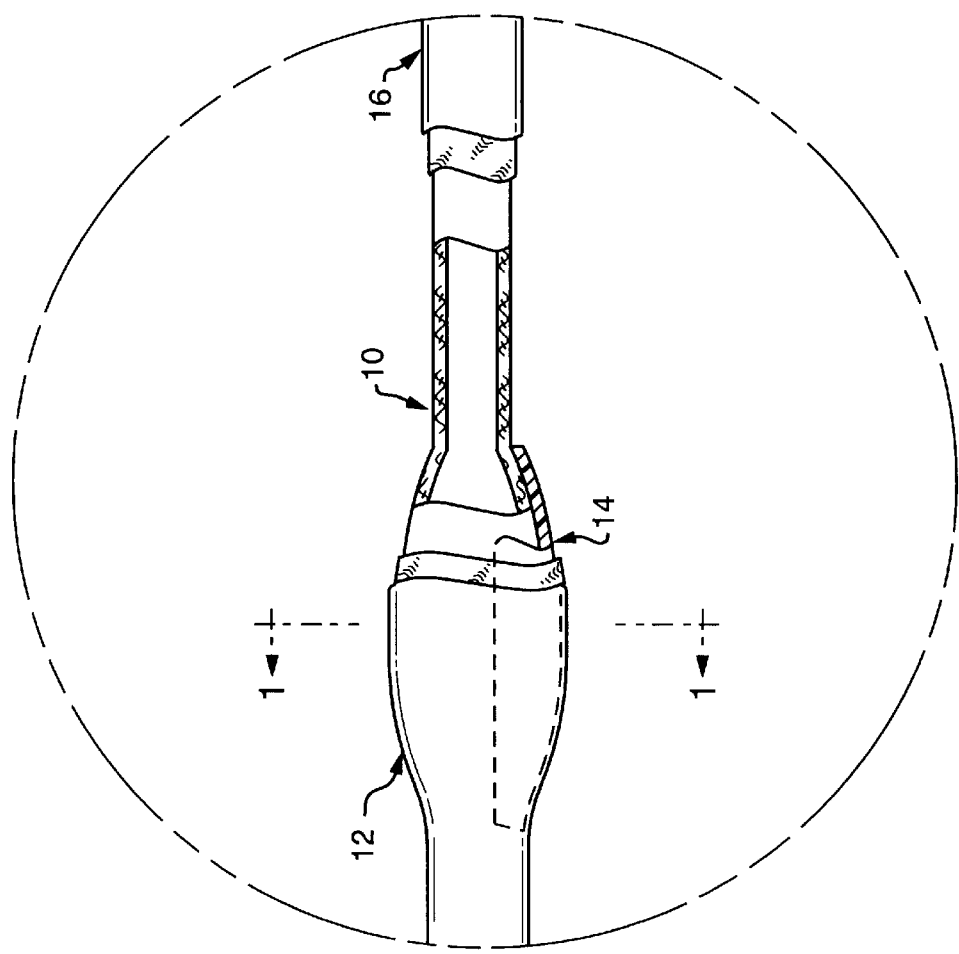
FIG. 2 is a partial cross-sectional view of the FIG. 1 view.

In FIGS. 1 and 2, a graft 1 comprises a tube 10 having a plurality of expanded regions 12. The non-expanded regions of tube 10 and each of the expanded regions 12 are accessible for cannulation by a needle. The tube 10 should be made of a material suitable to long term compatibility with human tissue, and such materials are well known in the art of graft design. The expanded regions 12 should be no greater in diameter than three times the non expanded regions of the tube 10. A desirable ratio of expanded regions 12 to non-expanded regions 10 is at or near (2 to 3):1.

An additional desirable feature comprises placement of a shield 14 at each expanded region. Shield 14 comprises a material less penetrable than the material of the tube 10 made of a biocompatible plasticized or metallic material. The greater difficulty in penetrability or impenetrability of shield 14 provides a means for alerting a physician, nurse, or medical technician that a needle cannulated into tube 10 is in danger of perforating and protruding through the tube 10 entirely. As the tip of a needle is pushed into the tube 10, a great resistance will be felt when shield 14 is contacted. This resistance will not only signal the physician, nurse, or medical technician to withdraw the needle slightly thereby ensuring that the needle tip remains within the graft 1, but will prevent the through and through penetration that actually tears or perforates the graft. In order for this feature to properly function, the graft 1 must be properly oriented with the patient. Proper orientation will ensure that the shields 14 are on the posterior aspect of the expanded portions 12 of the graft 1 as the graft is accessed by a needle. This could be readily accomplished by providing indicia on the graft which signifies proper orientation. Prior grafts make use of indicia and therefore this approach could be simply adapted for the present use.

The invention can be manufactured by unitary construction which means that shield 14 be incorporated into the tube 10 during the extrusion process typically used to form tube 10. However, the shields 14 could also be added to the tube 10 during assembly so long as they are bonded or otherwise made to remain in place. This can be accomplished by the addition of a suitable adhesive or by wrapping tube 10 and shields 14 with a bio-compatible cover or wrap 16 designed to tightly secure the shields in place. As shown in FIG. 3 wrap 16 can be one or more layers in thickness and could also be a supplement to the use of said adhesive.

Although Applicant believes that either the shield 14 or the expanded regions 12 of the tube 10 could be used separately, Applicant considers the best mode to include both. As such although the method of making and using the device detailed above constitute the inventor's preferred embodiment to the invention, the inventor is aware that numerous configurations are available which would provide the desired results. While the invention has been described and illustrated with reference to a specific embodiment, it is understood that these other embodiments may be resorted to without departing from the invention. Therefore the form of the invention set out above should be considered illustrative and not as limiting the scope of the following claims.

What is claimed is:

1. A medical graft comprising an implantable tube having a length and at least a first cross-sectional area and a plurality of regions defined by a substantially greater cross-sectional area than the first cross-sectional area, wherein said plurality of regions of greater cross-sectional area have a minimum diameter and a maximum diameter, wherein each of said regions progress gradually from said minimum diameter to said maximum diameter and back to said minimum diameter; and said plurality of regions further contain a shield in communication with said tube wherein said shield is substantially less penetrable than is said tube so that a needle cannulated into said tube will meet greater resistance when said needle impinges upon said shield and said shield is oriented at a substantially posterior aspect of said tube with respect to said needle penetration site so that said needle enters said tube at a location substantially diametrically opposite said shield.

2. A medical graft in accordance with claim 1 wherein said maximum diameter is no greater than about three times said minimum diameter.

3. A medical graft in accordance with claim 2 bearing indicia for ensuring proper orientation of said shield during placement of said graft in a patient.

4. A medical graft in accordance with claim 1 wherein said substantially greater cross-sectional area is no greater than about two to three times larger than said first cross-sectional area.

5. A medical graft in accordance with claim 4 bearing indicia for ensuring proper orientation of said shield during placement of said graft in a patient.

6. A bio-compatible graft for placement within a human comprising:

a tube having a minimum internal cross-sectional area and a length substantially greater than said minimum internal cross-sectional area, wherein said tube further comprises a plurality of spaced expanded regions thereon, each of said expanded regions having an internal cross-sectional area less than three times as large as said minimum internal cross-sectional area;

a plurality of shields, one for each expanded region, each shield is internally and integrally contained within said graft; and a cover, said cover encompassing and retaining therein said tube and said shields;

said plurality of shields each capable of signifying to a medical person that a needle cannulated into said expanded region from a position opposite said shield has contacted said shield, said plurality of shields to be oriented to a posterior aspect of said graft from a needle cannulation perspective.

7. A bio-compatible graft in accordance with claim 6 further comprising indicia for enabling a predetermined orientation of said graft within said human.

* * * * *